United States Patent
Magro et al.

(10) Patent No.: US 10,668,304 B2
(45) Date of Patent: Jun. 2, 2020

(54) PHANTOM FOR ADAPTIVE RADIOTHERAPY

(71) Applicant: Elekta, Inc., Atlanta, GA (US)

(72) Inventors: Nicolette Patricia Magro, Denver, NC (US); Xiao Han, Chesterfield, MO (US)

(73) Assignee: Elekta, Inc., Atlanta, GA (US)

( * ) Notice: Subject to any disclaimer, the term of this patent is extended or adjusted under 35 U.S.C. 154(b) by 131 days.

(21) Appl. No.: 15/966,830

(22) Filed: Apr. 30, 2018

(65) Prior Publication Data

US 2019/0329072 A1    Oct. 31, 2019

(51) Int. Cl.
| | | |
|---|---|---|
| *A61N 5/10* | (2006.01) | |
| *G01T 1/02* | (2006.01) | |
| *G01T 1/161* | (2006.01) | |

(52) U.S. Cl.
CPC .......... *A61N 5/1075* (2013.01); *A61N 5/1071* (2013.01); *G01T 1/02* (2013.01); *G01T 1/161* (2013.01); *A61N 5/1031* (2013.01); *A61N 5/1039* (2013.01); *A61N 2005/1034* (2013.01); *A61N 2005/1076* (2013.01)

(58) Field of Classification Search
CPC .. A61N 5/1031; A61N 5/1039; A61N 5/1071; A61N 5/1075; A61N 2005/1034; A61N 2005/1072; A61N 2005/1076; G01T 1/02; G01T 1/161

See application file for complete search history.

(56) References Cited

U.S. PATENT DOCUMENTS

| | | |
|---|---|---|
| 2008/0298540 A1 | 12/2008 | Serban et al. |
| 2014/0294140 A1* | 10/2014 | Kirby ............... A61B 6/032 378/18 |
| 2017/0018205 A1* | 1/2017 | Santhanam .......... G09B 23/286 |
| 2017/0042502 A1 | 2/2017 | Koo et al. |
| 2017/0050052 A1 | 2/2017 | Burgett et al. |

FOREIGN PATENT DOCUMENTS

| | | |
|---|---|---|
| EP | 2977008 | 1/2016 |
| WO | 2012075577 | 6/2012 |
| WO | 2014022480 | 2/2014 |

(Continued)

OTHER PUBLICATIONS

Roussakis, Yiannis G., "Strategies for adaptive radiotherapy: towards clinically efficient workflows", Diss. University of Birmingham, (2015), 224 pgs.

(Continued)

*Primary Examiner* — Mark R Gaworecki

(74) *Attorney, Agent, or Firm* — Schwegman Lundberg & Woessner, P.A.; Sanjay Agrawal

(57) ABSTRACT

A deformable radiotherapy phantom can be produced using an additive manufacturing process, based on a medical image of the patient. The deformable phantom can include dosimeters for measuring radiation dose distribution. A smart material can allow deformation in response to an applied stimulus. Among other things, the phantom can be used to validate radiation dose warping, a radiotherapy treatment plan, to determine a maximum acceptable deformation of the patient, to validate a cumulative accuracy of dose warping and deformable image registration, or the like.

17 Claims, 8 Drawing Sheets

(56) References Cited

FOREIGN PATENT DOCUMENTS

| WO | 2014165611 | 10/2014 |
|---|---|---|
| WO | 2015109121 | 7/2015 |

OTHER PUBLICATIONS

"International Application Serial No. PCT US2019 028724, International Search Report dated Aug. 13, 2019", 6 pgs.

"International Application Serial No. PCT US2019 028724, Written Opinion dated Aug. 13, 2019", 8 pgs.

Zhong, Hualiang, "Development of a deformable dosimetric phantom to verify dose accumulation algorithms for adaptive radiotherapy", Journal of Medical Physics, Medknow Publications and Media PVT. Ltd, IN, vol. 41, No. 2, (Jan. 1, 2016), 17 pgs.

* cited by examiner

PHANTOM FOR ADAPTIVE RADIOTHERAPY

TECHNICAL FIELD

This disclosure generally relates to radiotherapy. More specifically, but without limitation, the disclosure relates to the use of a phantom for quality assurance testing in radiotherapy.

BACKGROUND

Radiation therapy, also known as radiotherapy, is used to treat tumors and other ailments in mammalian (e.g., human and animal) tissue. In a radiotherapy treatment session, a high-energy beam is applied from an external source towards a patient to produce a collimated beam of radiation directed to a target site of a patient. The target may be a region of the patient's body that contains a diseased organ or tumor that is to be exposed to, and treated by, the radiation beam. The placement and dose of the radiation beam must be accurately controlled to ensure that the target receives the dose of radiation that has been prescribed for the patient by a physician. The placement of the beam should be such that it minimizes damage to the surrounding healthy tissue, often called the organ(s) at risk (OARs).

One way to improve the accuracy of the beam placement is by the acquisition of one or more medical images of the patient in the intended treatment position. Such images are known as planning images. The planning images are acquired prior to a radiotherapy treatment session, and are often acquired many days before the treatment session.

Physicians can use the planning images to identify and contour a target as well as OARs. Contouring can be performed manually, semi-automatically, or automatically. A treatment contour, often referred to as a planned target volume (PTV), is created which includes the target contour plus sufficient margins to account for microscopic disease as well as treatment uncertainties. A radiation dose is prescribed by the physician, and a radiotherapy treatment plan is created that optimally delivers the prescribed dose to the PTV while minimizing dose to the OARs and other normal tissues. The treatment plan can be generated manually by the physician, or can be generated automatically using an optimization technique. The optimization technique may be based on clinical and dosimetric objectives and constraints (e.g., the maximum, minimum, and mean doses of radiation to the tumor and OARs).

A treatment course is developed to deliver the prescribed dose over a number of fractions, wherein each fraction is delivered in a different treatment session. For example, 30-40 fractions are typical, but five or even one fraction can be used. Fractions are often delivered once, or in some cases twice, per weekday. In some cases, the radiation treatment plan can change throughout the course to focus more dose in some areas.

In each fraction, the patient is set up on a patient support accessory (often a "couch") of a radiotherapy device, and repositioned as closely as possible to their position in the planning images. This is a difficult task to carry out accurately in practice, because the patient is not a rigid object and the patient's anatomy can move. Fraction-to-fraction motions are often referred to as interfractional motion, while motion occurring during a fraction itself is often referred to as intrafractional motion.

Image-guided radiotherapy (IGRT) attempts to solve the problem of interfractional motion. IGRT involves acquiring one or more medical images of the patient shortly before radiotherapy (often referred to as "daily images"), and using those images to identify and compensate for interfractional motion. As opposed to planning images, which can be acquired on any diagnostic scanner, IGRT images are acquired directly in the treatment room, while the patient is in the treatment position. To compensate for interfractional motion, IGRT images are compared with the planning images to quantify changes in the patient's anatomy that have occurred since the planning images were generated. For example, the planning images and IGRT images may be analyzed to calculate a global shift and/or rotation that maps the planning images to the IGRT images. Once the shift and/or rotation have been calculated, a corresponding adjustment to the position of the patient support accessory can be made, such that the position of the patient during the treatment session more closely matches the position of the patient when the planning images were acquired.

Adaptive radiotherapy is another technique that aims to solve the problem of interfractional motion. As with IGRT, adaptive radiotherapy involves acquiring one or more medical images of the patient shortly before a radiotherapy treatment session, and using those images to identify and compensate for interfractional motion. In adaptive radiotherapy, the planning images and the images taken shortly before the treatment session may be analyzed to generate a deformation vector field (DVF). The DVF is a matrix whose elements are vectors, and in which each vector defines a geometric transformation to map a voxel in a planning image to a corresponding voxel in an image taken shortly before the treatment session. The DVF can be used to transform the spatial distribution of the radiation dose prescribed by a treatment plan, in order to compensate for changes in the patient's anatomy that have occurred since the planning images were acquired.

Transforming the dose distribution in this manner may result in the target receiving less than the prescribed dose and/or an OAR being exposed to a higher level of radiation than the physician intended. There is thus a need to verify that a transformed dose distribution is clinically effective and safe.

SUMMARY

A deformable radiotherapy phantom can be produced using an additive manufacturing process, based on a medical image of the patient. The deformable phantom can include dosimeters for measuring radiation dose distribution. A smart material can allow deformation in response to an applied stimulus. Among other things, the phantom can be used to validate radiation dose warping, a radiotherapy treatment plan, to determine a maximum acceptable deformation of the patient, to validate a cumulative accuracy of dose warping and deformable image registration, or the like.

Additional advantages of the present disclosure will be set forth in part in the following detailed description, and in part will be apparent from the description, or may be learned by practice of the present disclosure.

It is to be understood that the foregoing general description and the following detailed description are exemplary and explanatory only, and are not restrictive of the invention, as claimed.

BRIEF DESCRIPTION OF THE DRAWINGS

The accompanying drawings, which constitute a part of this specification, illustrate several embodiments and, together with the description, serve to explain the disclosed principles.

DETAILED DESCRIPTION

Figure 1A:
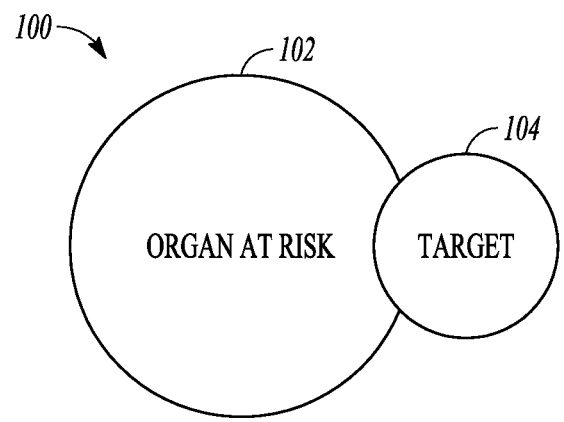
FIGS. 1A, 1B and 1C are plan, front and side views, respectively, of a region of interest of a patient.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

Exemplary embodiments generally relate to the use of a phantom for quality assurance in adaptive radiotherapy. As explained in more detail below, a phantom is produced using a medical image of a patient, thus resulting in a phantom that closely reflects the anatomy of the specific patient that is to be treated by radiotherapy. A plurality of dosimeters may be positioned within the phantom, thus allowing radiation dose to be measured at several points within the internal volume of the phantom, which in turn allows prediction of the spatial distribution of the dose that the patient will receive. In some embodiments, the phantom is deformable so as to allow the effects of patient motion upon dose distribution to be modelled. A plurality of such phantoms can be produced, each phantom being produced using different medical images of the patient. The dose distributions received by each phantom can be compared in order to verify, for example, a treatment plan for adaptive radiotherapy or a deformable image registration algorithm that is used to generate a deformation vector field for adaptive radiotherapy.

In the field of radiotherapy, a "phantom" is an object that is used as a substitute for a patient's body, or a portion of a patient's body. Phantoms are typically used to test radiotherapy treatment plans. For example, a beam of radiation may be applied to the phantom in accordance with a treatment plan, and the radiation passing through the phantom may be measured by a detector positioned opposite the beam. The radiation dose received by the phantom can be inferred from the detector measurements. The clinical efficacy and safety of the treatment plan can be determined by comparing the prescribed dose (that is, the dose that the treatment plan was intended to deliver) with the dose that was actually received by the phantom. A phantom thus allows a treatment plan to be tested without exposing the patient to radiation.

Figure 1B:
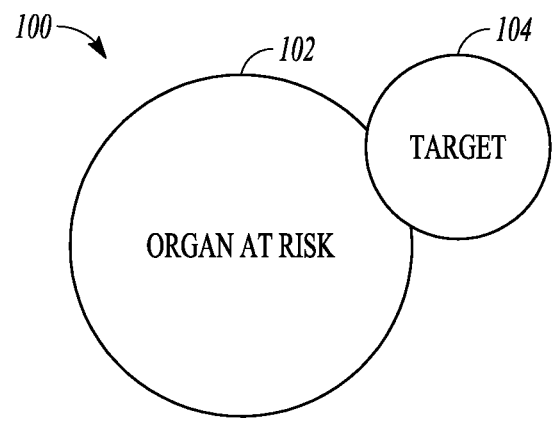
Figure 1C:
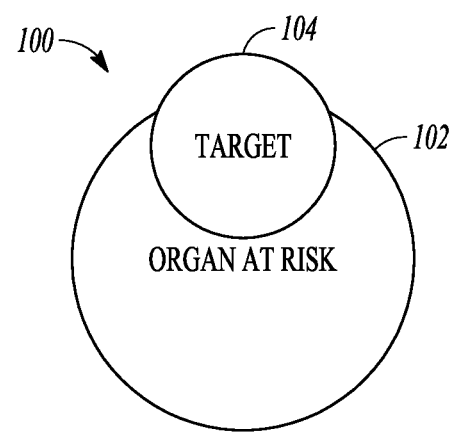

A phantom in accordance with the present disclosure will now be described with reference to FIGS. 1 and 2. FIGS. 1A, 1B and 1C are schematic diagrams of a region of interest 100 of a patient, depicted in three mutually orthogonal directions. More specifically, FIG. 1A is a plan view of the region of interest 100, FIG. 1B is a front view of the region of interest 100, and FIG. 1C is a side view of the region of interest 100. The region of interest 100 includes an organ at risk (OAR) 104 and a target 104. It will be appreciated that FIG. 1 is a very simplified representation of a region of interest, and is intended purely for the purposes of explanation. In reality, an OAR 102 and an target 104 may have highly irregular shapes. Furthermore, in reality, a region of interest 100 may have multiple OARs, other non-target regions, and/or multiple targets.

In accordance with the present disclosure, a phantom of the region of interest 100 is produced using a medical image of a patient. The medical image is a three-dimensional image (also known as a volumetric image), which is composed of a plurality of elements known as voxels. Each voxel represents the intensity of the image at a particular point in three-dimensional space. Any suitable imaging modality can be used to acquire the medical image, such as computed tomography (CT), magnetic resonance imaging (MRI), positron emission tomography (PET), ultrasound, or single photon emission computerized tomography (SPECT). Alternatively, the medical image may be generated by fusing images acquired using two or more different imaging modalities. The medical image that is used to produce the phantom may be an image that has been acquired for the purposes of radiotherapy itself. For example, a planning image or a daily image can be used to produce the phantom. This can avoid the need for an image to be acquired solely for the purpose of producing the phantom.

The medical image is segmented into a target region and at least one non-target region. Segmentation generally refers to a process of assigning labels to voxels in an image in order to denote what those voxels represent. Thus, the target region includes a plurality of voxels that are labelled as a target 104 to be treated by exposure to radiation. Each non-target region includes a plurality of voxels that are labelled as something other than the target 104. For example, a non-target region may include voxels that that are labelled as an organ at risk 102. The medical image may include one or more organs at risk. As another example, a non-target region may include voxels that are labelled as background voxels, i.e. voxels that do not represent the body of the patient. The medical image may have been segmented manually (e.g., by a physician, dosimetrist, or health care worker) or automatically (e.g., using a program such as the Atlas-based auto-segmentation software, ABAS®, manufactured by Elekta AB of Stockholm, Sweden).

A phantom can be produced by an additive manufacturing process, such as based upon a medical image of a region of interest of the patient. The region of interest can include a target region and the non-target region. The first and second portions of the phantom can each have a respective shape defined by the shape of the target region and the non-target region, respectively, in the medical image.

After imaging, an additive manufacturing process can then be used to create a three-dimensional phantom that models the anatomical structures in the three-dimensional medical image. As used herein, the term "additive manufacturing" refers to a process by which an object is manufactured in a layer by layer manner. According to the American Society for Testing and Materials (ASTM), seven types of additive manufacturing process currently exist: binder jetting; directed energy deposition; material extrusion, also known as fused deposition modeling; material jetting; powder bed fusion; sheet lamination; and vat photopolymerization. Any suitable one or more of these types of additive manufacturing processes, or any other suitable type of additive manufacturing process that may exist in the future, can be used to produce the phantom. Further, any suitable software tool(s) can be used to convert the three-dimensional medical image into instructions and/or data that an additive manufacturing device can use to produce a phantom that replicates the anatomical structures in the medical image.

Figure 2A:
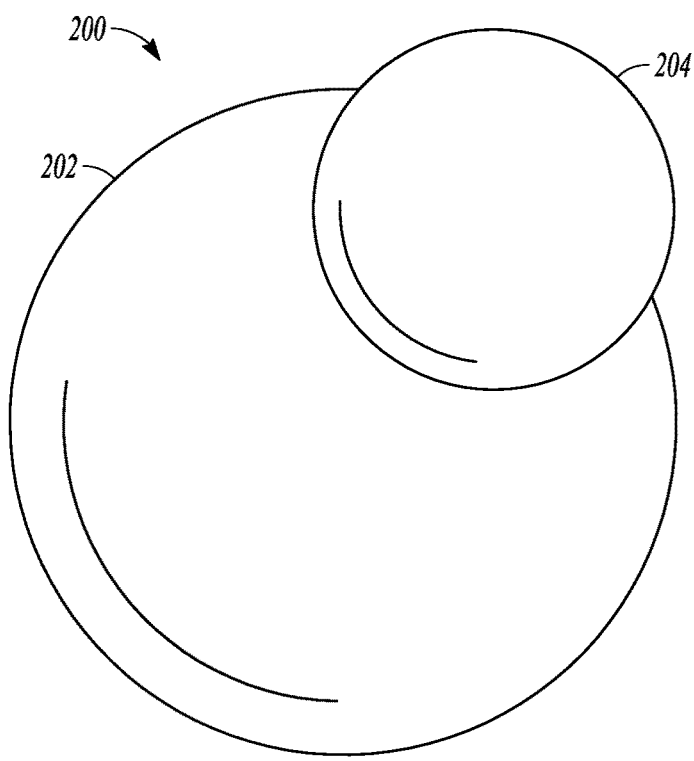
FIG. 2A is a perspective view of a phantom for modelling the region of interest shown in FIGS. 1A to 1C.

FIG. 2A is a perspective view of a phantom 200 for modelling the region of interest shown in FIGS. 1A to 1C. As can be seen from FIG. 2A, the phantom 200 is a three-dimensional physical object that represents the anatomy of the region of interest. The phantom comprises a portion 202 that represents the OAR 102, and a portion 204 that represents the target 104. It will be appreciated that FIG. 2 is a very simplified representation of a phantom 200 and, in reality, the phantom has a more complex shape that reflects the anatomy of a patient. Furthermore, the phantom 200 may comprise a greater number of portions than shown in FIG. 2A.

The phantom 200 comprises one or more materials whose radiation absorption properties are similar, or identical, to those of the anatomical structures in the region of interest 100. For example, portion 202 of the phantom 200 may comprise a material having a density similar to that of an organ (such as a prostate, bladder, brain, etc.), whilst portion 204 of the phantom 200 may comprise a material having a density that is similar to that of a tumor. The phantom 200 can thus be used to predict the radiation dose that will be absorbed by the corresponding anatomical structures of the patient during radiotherapy. The constituent materials of the phantom 200 may be selected based upon both their radiation absorption properties and their suitability for use with a particular additive manufacturing process. Multiple materials may be combined in order to produce a phantom 200 that has the desired radiation absorption properties and that is capable of being produced by a given additive manufacturing process. For example, the portions 202, 204 may be produced by forming hollow polymer shells using additive manufacturing, and then filling the shells with materials whose density is similar to that of the respective anatomical structure 102, 104.

In some embodiments, the phantom 200 may be deformable. Deformation of the phantom 200 allows movement of the OAR 102 and/or target 104 to be modelled. Possible causes of movement of the OAR 102 and/or target 104 that can be modelled by deformation of the phantom 200 include, for example: physiological processes, such as breathing, emptying of the bladder and/or bowel, and filling of the bladder and/or bowel; weight loss or weight gain of the patient; growth of the target 104 due to disease progression; and shrinkage of the target 104 due to successful radiotherapy. The phantom 200 can be deformed in a manner that accurately reflects the actual movement of the OAR 102 and/or target 104 by producing the phantom using one or more deformable materials (such as elastomeric materials), and by applying forces to the phantom to cause movement of the portions 202, 204. Either, or both, of the portions 202, 204 can be deformable.

In some embodiments, deformation of the phantom 200 can be achieved by producing the phantom using one or more smart materials. A smart material is a material that exhibits a predictable and controllable change in shape when exposed to an external stimulus. For example, there exist smart materials whose shape changes when exposed to stimuli such as humidity, temperature, light, electric fields or magnetic fields. Furthermore, a number of so-called "4D printing" materials exist, which are smart materials that can be used in an additive manufacturing process. The smart material and/or the properties (e.g. amplitude, frequency, etc.) of the stimulus that is applied thereto can be selected so as to cause the phantom 200 to deform in a manner that models movement of the OAR 102 and/or target 104. Either, or both, of the portions 202, 204 can comprise a smart material.

The phantom 200 comprises a plurality of radiation dosimeters. The dosimeters may be positioned within the phantom 200. More particularly, the plurality of dosimeters may be distributed throughout the internal volume of the phantom 200. This can allow radiation dose to be measured at several points in space, thereby allowing the spatial distribution of the dose received by the phantom 200 to be determined. This in turn allows the phantom 200 to be used to accurately predict the dose that will be received by the OAR 102 and target 104 during radiotherapy. Dosimeters may also be positioned on an external surface of the phantom 200. The dosimeters may comprise any suitable device that is capable of measuring a radiation dose. For example, the dosimeters may include an electronic dosimeter, such as a metal oxide semiconductor field effect transistor (MOSFET) dosimeter. Alternatively or additionally, the dosimeters may include a thermoluminescent dosimeter (TLD), or a chemical having a property (e.g. color) that changes when exposed to radiation.

Figure 2B:
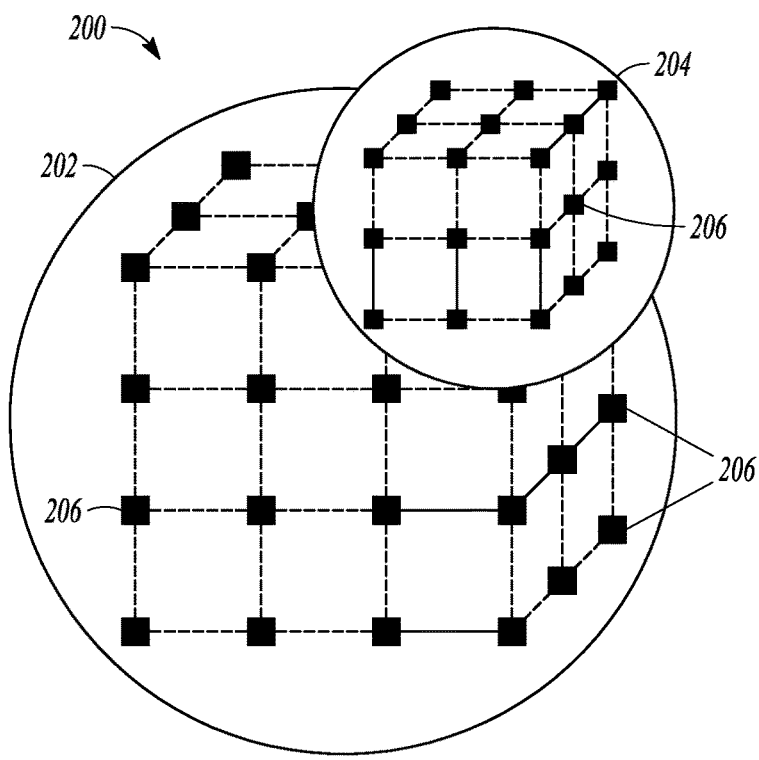
FIG. 2B is a schematic diagram illustrating the placement of dosimeters within the phantom of FIG. 2A.

FIG. 2B is a schematic diagram that exemplifies the placement of dosimeters 206 within the phantom 200 of FIG. 2A. FIG. 2B shows the portions 202 and 204 in cross-section, so as to allow the spatial distribution of the dosimeters 206 to be seen. As shown in FIG. 2B, a plurality of dosimeters 206 are distributed throughout the internal volume of each portion 202, 204 of the phantom 200. The dosimeters 206 may be uniformly distributed throughout the internal volume of the phantom 200. For example, in FIG. 2B, the dosimeters 206 are positioned on the nodes of the three-dimensional grid that is illustrated by dashed lines. However, the dosimeters 206 need not be uniformly distributed throughout the internal volume of the phantom 200. For example, a greater number of dosimeters 206 per unit volume may be used in regions where it is desired to measure dose with a higher spatial resolution (e.g. near the boundary of the OAR 102 and the target 104), and a lower number of dosimeters 206 per unit volume may be used elsewhere. As another example, a non-uniform distribution of dosimeters may result from deforming the phantom 200. The dosimeters 206 can be automatically positioned in the phantom 200 during the additive manufacturing process, or can be added to the phantom after the additive manufacturing process is completed.

The phantom described above can be used for a variety of quality assurance tests. In the field of radiotherapy, quality assurance (QA) generally refers to procedures for ensuring that a patient receives the radiation dose that has been prescribed.

Figure 3:
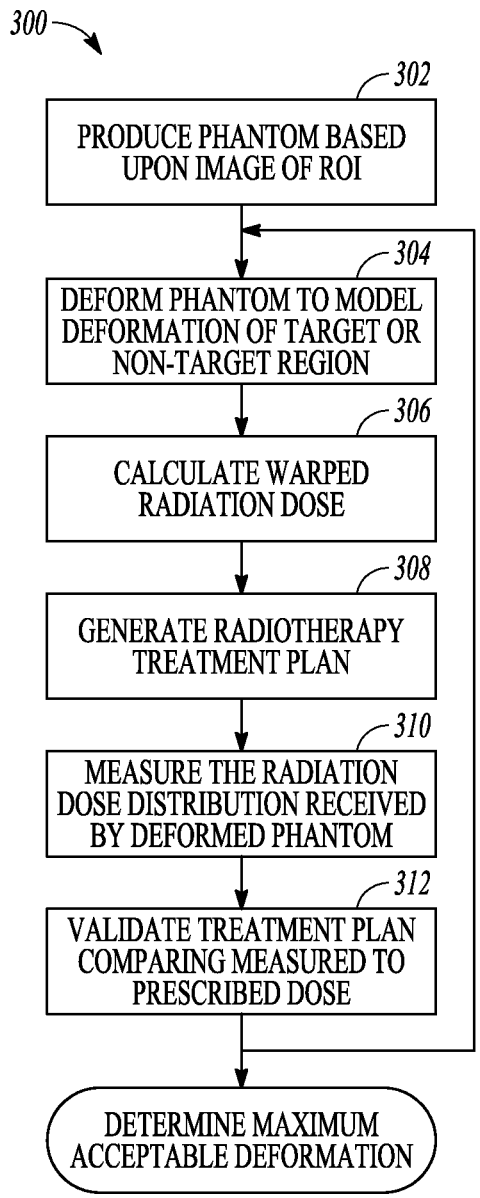
FIG. 3 illustrates an example of a validation or quality assurance test method for which the phantom can be used.

FIG. 3 illustrates an example of a quality assurance test method 300 for which the phantom can be used. At 302, a phantom based upon a medical image of a region of interest (ROI) of a patient can be produced or obtained. The ROI can include a target region to be treated by radiotherapy and a non-target region, such as can include an organ at risk (OAR) to which radiotherapy treatment is to be avoided. The phantom can be produced by 3D printing or other additive manufacturing process, such as described herein. The phantom can be deformable, such as in a similar manner to a portion of a patient that will undergo radiotherapy treatment, which may involve positioning or re-positioning the patient on a radiation couch, or other movement or deformation of the patient, such as via breathing, or the like. In an example, the phantom can include a plurality of radiation dosimeters included or distributed therewithin.

At 304, the phantom can be deformed, such as to model a deformation of at least one or both of the target region or the non-target region of the patient. This deformation can include applying a physical force to the phantom, such as to compress, stretch, twist, or otherwise deform the phantom in a matter similar to an expected, predicted, or measured deformation of a corresponding region of the patient. In an example, the phantom can include a "smart" material that exhibits a change in shape when exposed to an external stimulus, in which case, deforming the phantom can include applying the external stimulus to the smart material.

At 306, a warped radiation dose can be calculated, such as by applying a geometric transformation to a prescribed radiation dose. The prescribed radiation dose can define an intended spatial distribution of radiation to be delivered to the ROI of the patient. The prescribed radiation dose can be included as part of a treatment plan for the patient, such as can be created such as can include using a Monte Carlo dose calculation technique in a Monaco treatment planning system (TPS) available from Elekta AB, of Sweden. The intended spatial distribution of radiation of the prescribed radiation dose can be geometrically transformed.

In an example, the geometric transformation can optionally include applying a deformation matrix that can be generated by: (1) acquiring an image of the phantom prior to deforming the phantom; (2) acquiring an image of the deformed phantom; and (3) calculating the geometric transformation based upon the image of the undeformed phantom and the image of the deformed phantom.

For example, the image of the undeformed phantom and the image of the deformed phantom can each include a plurality of voxels, and calculating the geometric transformation can include performing a deformable image registration to calculate a deformation vector field matrix that maps each voxel in the image of the phantom to a corresponding voxel in the image of the deformed phantom.

At 308, a radiotherapy treatment plan for configuring a radiotherapy apparatus to deliver the warped radiation dose can be generated, created such as can include using a Monte Carlo dose calculation technique applied to generate the warped radiation dose, e.g., such as using a Monaco treatment planning system (TPS) available from Elekta AB, of Sweden.

At 310, a measurement can be obtained of the radiation dose distribution received by the deformed phantom, such as when radiation is delivered to the deformed phantom by operating the radiotherapy apparatus in accordance with the radiotherapy treatment plan. Such measurement can be obtained using the plurality of dosimeters included or distributed within the deformed phantom.

At 312, the radiotherapy treatment plan can be validated by comparing the measured radiation dose distribution with the prescribed radiation dose. This can include computing a similarity or difference metric between the measured and prescribed radiation dose distribution, and affirming the treatment plan when the similarity between the measured and prescribed radiation dose distributions exceeds a specified similarly sufficiency value, or when a difference between the measured and prescribed radiation dose is less than a specified difference sufficiency value. One or more other metrics can additionally or alternatively be used to validate the radiotherapy treatment plan, for example, if an aggregate or other radiation exposure of one or more organs at risk (OARs) exceeds a maximum acceptable value.

Acts 304-312 can optionally be repeated, such as with different deformations applied at 304 to the deformable phantom. By validating at 312 using different deformations applied at 304, at 314 a maximum acceptable deformation of at least one of the target region or the non-target region for which the radiotherapy treatment plan is valid, can be determined. For example, when incrementally increasing the recurring deformations at 304, when the deformation is increased beyond a certain value, the similarity metric between the measured and prescribed radiation doses may eventually fall below a specified acceptable similarity limit, or a difference metric may eventually exceed a specified acceptable difference limit, such that the previous (acceptable) deformation in the recurrently increasing series of deformations can be declared as the maximum acceptable deformation.

Figure 4:
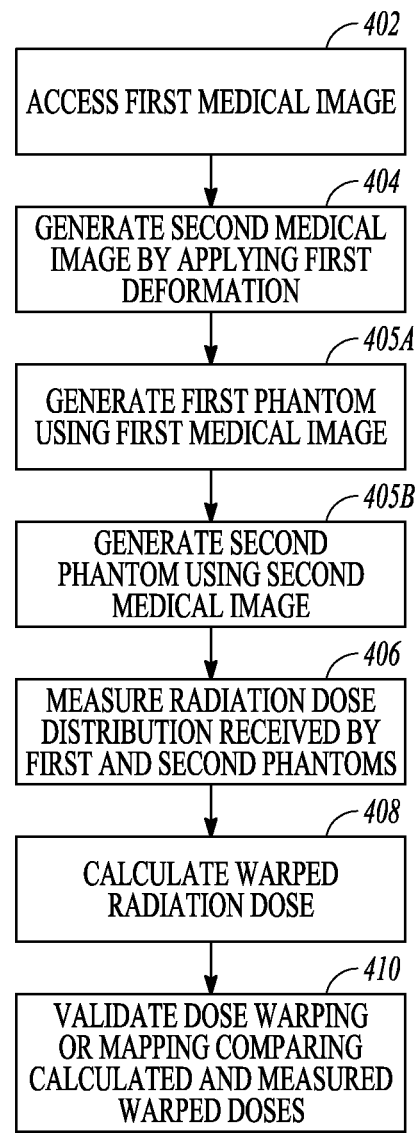
FIG. 4 illustrates an example of a method of validating a dose mapping algorithm.

FIG. 4 illustrates an example of a method 400 of validating a dose mapping algorithm. At 402, a first medical image representing an ROI of a patient can be accessed, such as by image processing circuitry accessing a medical imaging database including voxel data obtained using an imaging modality. At 404, a second medical image can be generated using the first medical image, such as by applying a first deformation vector field to the first medical image to generate the second medical image. At 405A, a first phantom can be obtained, provided, or generated (e.g., such as can include using 3D printing or other additive manufacturing process) such as in accordance with the first medical image. At 405B, a (deformed) second phantom can be obtained, provided, or generated (e.g., such as can include using 3D printing or other additive manufacturing process) such as in accordance with the (deformed) second medical image. At 406, a radiation dose distribution received by at least one phantom can be measured, such as in response to radiation delivered to the phantom by operating a radiotherapy apparatus, such as in accordance to a radiotherapy treatment plan. In an example, the at least one phantom can include first and second phantoms. In an example, the at least one phantom can be manufactured using 3D printing or other additive process, such as with a plurality of dosimeters included or distributed therewithin. At 408, the image processing circuitry can be used to calculate a warped radiation dose, such as by applying the first deformation vector field to the measured radiation dose distribution using a dose warping or mapping technique to be validated. At 410, an accuracy or other attribute of the dose warping or mapping technique to be validated can be validated by comparing the calculated dose distribution with the measured radiation dose distribution on the same phantom. This can include computing a voxel-by-voxel or aggregate composite similarity or difference metric therebetween, and comparing the similarity or difference metric to a corresponding threshold value to determine whether the metric falls within an acceptable range to validate the accuracy of the dose warping or mapping technique. A combination of voxel-by-voxel and composite validation can additionally or alternatively be used, e.g., if a difference or error metric for any voxel falls outside of a corresponding first acceptable range, or if a composite difference or error metric falls outside of a corresponding second acceptable range, the dose warping or mapping technique can be declared invalid. Additionally or alternatively, a more complex set of validation rules can be applied, for example, statistical metrics can be computed differently for different density regions for which the warped radiation dose distribution is being measured or calculated. Such density information can be obtained from the medical image data, for example.

Figure 5:
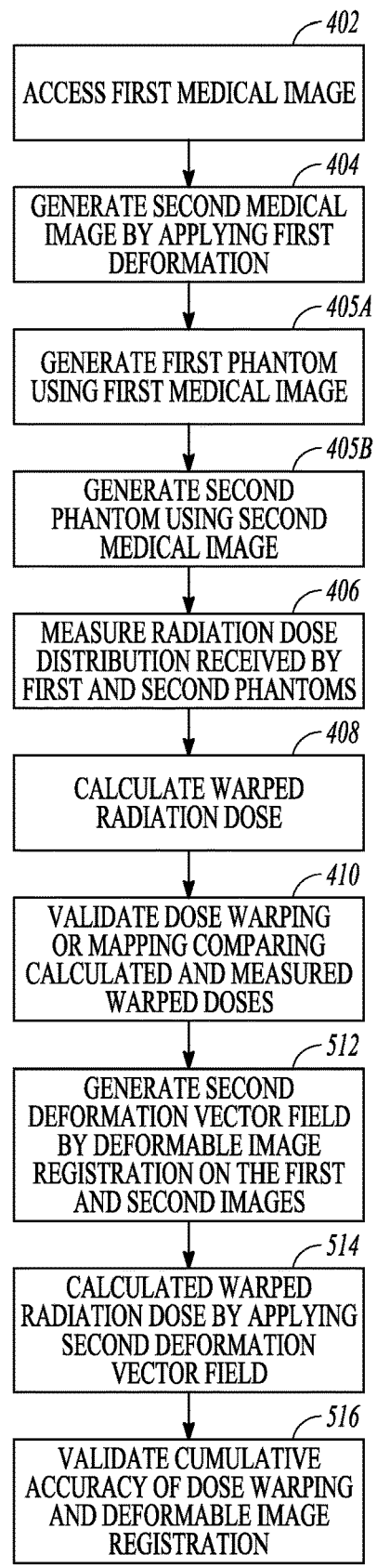
FIG. 5 illustrates an example of a further validation method.

FIG. 5 illustrates an example of a further method 500 of optionally validating a cumulative accuracy of dose warping and deformable image registration. Steps 402-410 can be performed as described above with respect to FIG. 4.

At 512, optionally a second deformation vector field can be generated, such as by performing a deformable image registration on the first and second medical images. This can include mapping individual voxels (e.g., each individual voxel) in the first medical image to a corresponding voxel in the second medical image.

At 514, optionally a warped radiation dose distribution can be calculated such as by applying the second deformation vector field generated at 410.

At 516, optionally a validation can be carried out of the cumulative accuracy of the calculated warped radiation dose distribution calculated at 414 and the deformable image registration of the first and second medical images used to generate the second deformation vector field. This validation can compare the measured radiation dose distribution of 406 to the calculated warped radiation dose calculated at 414 using the second deformation vector field based on the deformable image registration. As explained elsewhere herein, this validation can include computing a voxel-by-voxel or aggregate composite similarity or difference metric therebetween, and comparing the similarity or difference metric to a corresponding threshold value to determine whether the metric falls within an acceptable range to validate the accuracy of the dose warping or mapping technique. A combination of voxel-by-voxel and composite validation can additionally or alternatively be used, e.g., if a difference or error metric for any voxel falls outside of a corresponding first acceptable range, or if a composite difference or error metric falls outside of a corresponding second acceptable range, the dose warping or mapping technique can be declared invalid. Additionally or alternatively, a more complex set of validation rules can be applied, for example, statistical metrics can be computed differently for different density regions for which the warped radiation dose distribution is being measured or calculated. Such density information can be obtained from the medical image data, for example.

Figure 6:
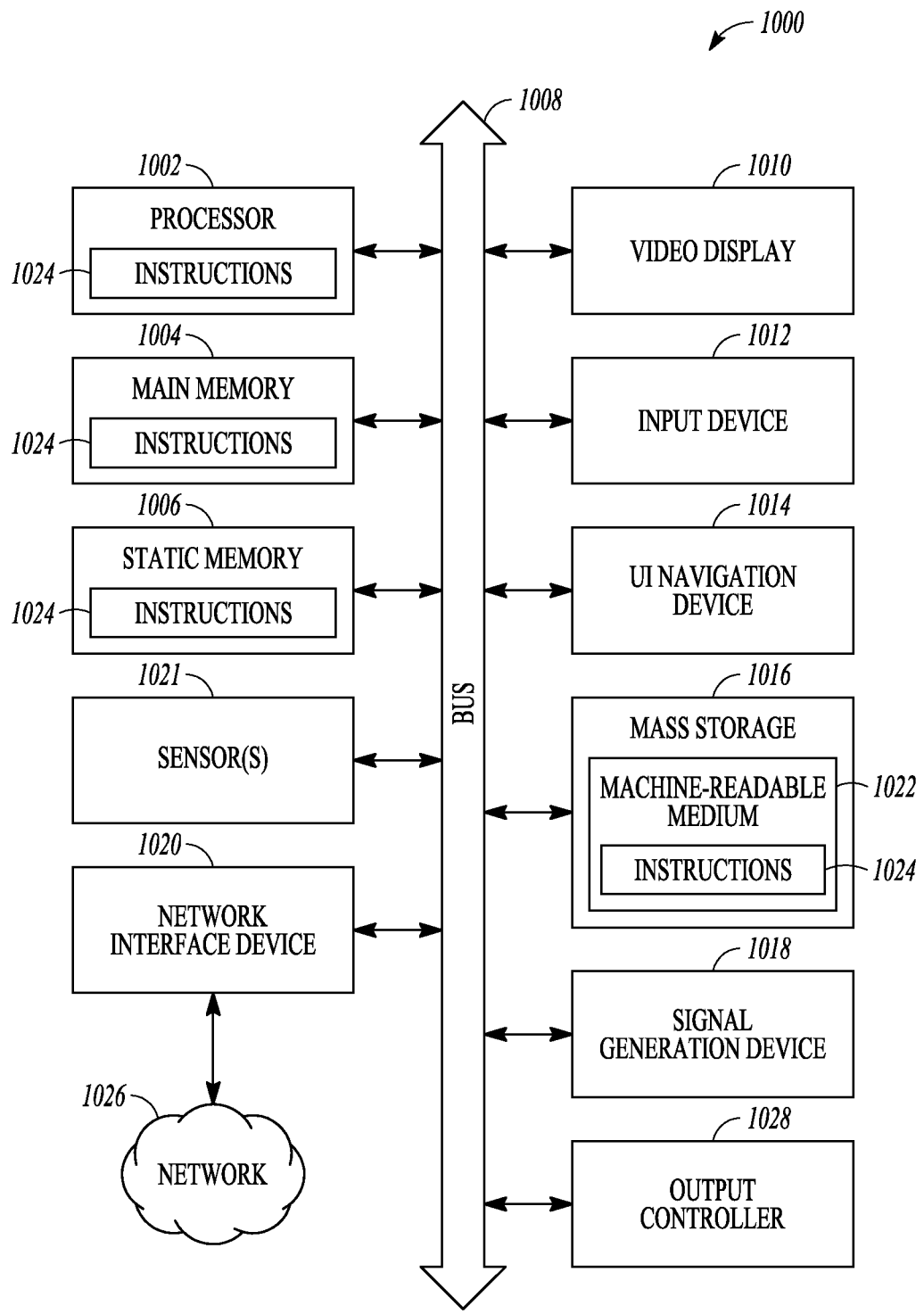
FIG. 6 illustrates a block diagram of an embodiment of a device or machine on which one or more of the methods as discussed herein can be implemented, such as for validating dose warping, deformable image registration, or the like, such as described herein.

FIG. 6 illustrates a block diagram of an embodiment of a device or machine 1000 on which one or more of the methods as discussed herein can be implemented. One or more items of the image processing circuitry described herein can be implemented by the machine 1000. The machine 1000 can operate as a standalone device or may be connected (e.g., networked) to other machines. The image processing circuitry can include one or more of the items of the machine 1000. In a networked deployment, the machine 1000 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 1000 can include processing circuitry 1002 (e.g., a central processing unit (CPU), a graphics processing unit (GPU), an application specific integrated circuit, circuitry, such as one or more transistors, resistors, capacitors, inductors, diodes, logic gates, multiplexers, buffers, modulators, demodulators, radios (e.g., transmit or receive radios or transceivers), sensors 1021 (e.g., a transducer that converts one form of energy (e.g., light, heat, electrical, mechanical, or other energy) to another form of energy), or the like, or a combination thereof), a main memory 1004 and a static memory 1006, which communicate with each other via a bus 1008. A datum or data associated with the described methods can be stored in or retrieved from such memory, and initialized or updated as desired to carry out the methods described herein. The machine 1000 (e.g., computer system) may further include a video display unit 1010 (e.g., a liquid crystal display (LCD) or a cathode ray tube (CRT)). The machine 1000 can also include an alphanumeric input device 1012 (e.g., a keyboard), a user interface (UI) navigation device 1014 (e.g., a mouse), a disk drive or mass storage unit 1016, a signal generation device 1018 (e.g., a speaker) and a network interface device 1020.

The disk drive unit 1016 can include a machine-readable medium 1022 on which is stored one or more sets of instructions and data structures (e.g., software) 1024 embodying or utilized by any one or more of the methodologies or functions described herein. The instructions 1024 may also reside, completely or at least partially, within the main memory 1004 and/or within the processor 1002 during execution thereof by the machine 1000, the main memory 1004 and the processor 1002 also constituting machine-readable media.

The machine 1000 as illustrated can include an output controller 1028. The output controller 1028 manages data flow to/from the machine 1000. The output controller 1028 can sometimes be called a device controller, with software that directly interacts with the output controller 1028 being called a device driver.

While the machine-readable medium 1022 is shown in an embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

The instructions 1024 may further be transmitted or received over a communications network 1026 using a transmission medium. The instructions 1024 may be transmitted using the network interface device 1020 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

Figure 7:
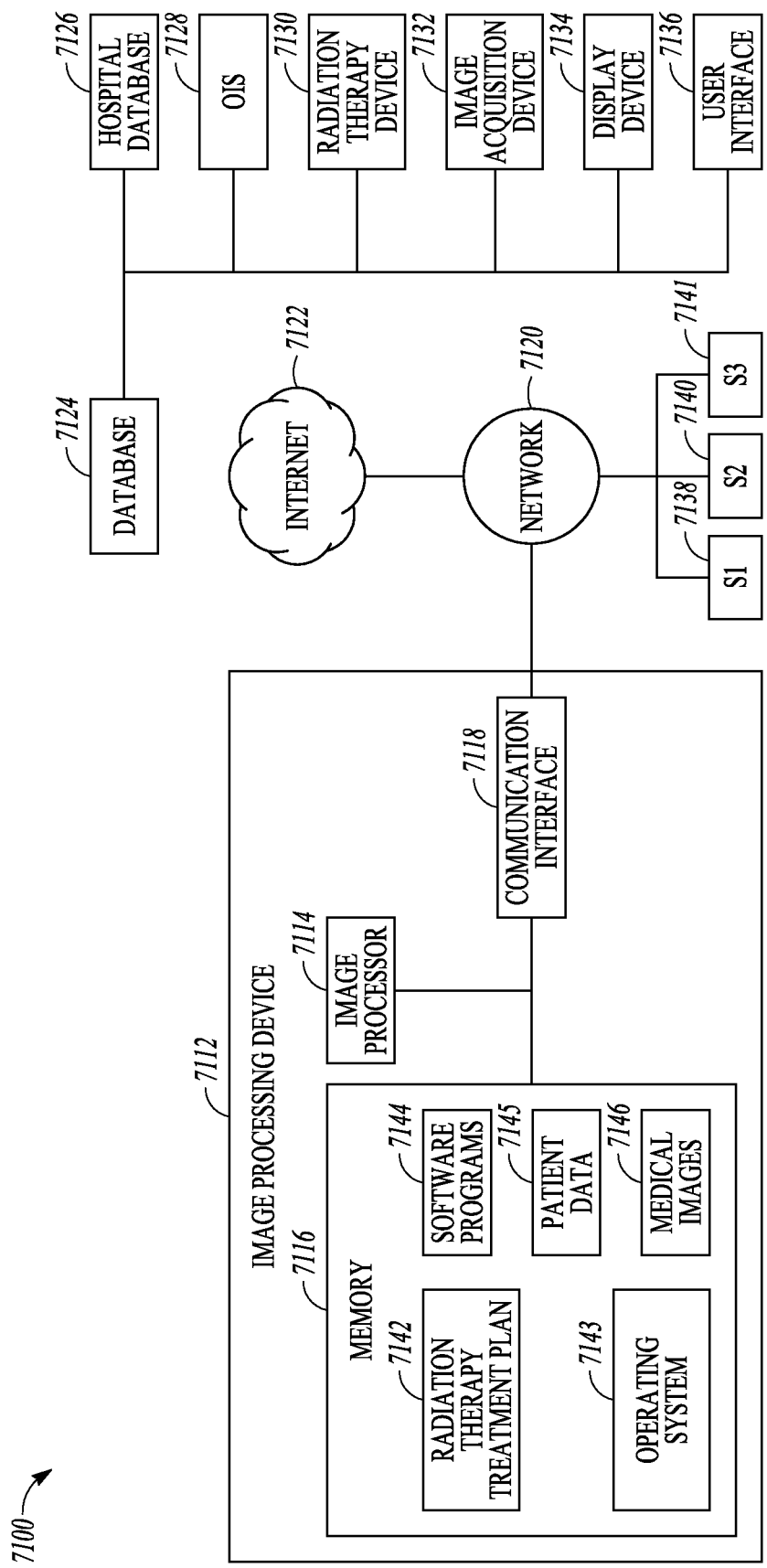
FIG. 7 illustrates an example of a radiotherapy system.

FIG. 7 illustrates an exemplary radiotherapy system 100 for providing radiation therapy to a patient, to a portion of a patient, or to a "phantom", which can include a target object representing the patient or the portion of the patient. The radiotherapy system 7100 includes an image processing device, 7112. The image processing device 7112 may be connected to a network 7120. The network 7120 may be connected to the Internet 7122. The network 7120 can connect the image processing device 7112 with one or more of a database 7124, a hospital database 7126, an oncology information system (01S) 7128, a radiation therapy device 7130, an image acquisition device 7132, a display device 7134, and a user interface 7136. The image processing device 7112 can be configured to generate radiation therapy treatment plans 7142 to be used by the radiation therapy device 7130.

The image processing device 7112 may include a memory device 7116, a processor 7114 and a communication interface 7118. The memory device 7116 may store computer-executable instructions, such as an operating system 7143, a radiation therapy treatment plans 7142 (e.g., original treatment plans, adapted treatment plans and the like), software programs 7144 (e.g., artificial intelligence, deep learning, neural networks, radiotherapy treatment plan software), and any other computer-executable instructions to be executed by the processor 7114. In one embodiment, the software programs 7144 may convert medical images of one format (e.g., MRI) to another format (e.g., CT) by producing synthetic images, such as a pseudo-CT image. For instance, the software programs 7144 may include image processing programs to train a predictive model for converting a medial image 7146 in one modality (e.g., an MRI image) into a synthetic image of a different modality (e.g., a pseudo CT image); alternatively, the trained predictive model may convert a CT image into an MRI image. In another embodiment, the software programs 7144 may register the patient image (e.g., a CT image or an MR image) with that patient's dose distribution (also represented as an image) so that corresponding image voxels and dose voxels are associated appropriately by the network. In yet another embodiment, the software programs 7144 may substitute functions of the patient images such as signed distance functions or processed versions of the images that emphasize some aspect of the image information. Such functions might emphasize edges or differences in voxel textures, or any other structural aspect useful to neural network learning. In another embodiment, the software programs 7144 may substitute functions of the dose distribution that emphasize some aspect of the dose information. Such functions might emphasize steep gradients around the target, or any other structural aspect useful to neural network learning. The memory device 7116 may store data, including medical images 7146, patient data 7145, and other data required to create and implement a radiation therapy treatment plan 7142.

In addition to the memory 4116 storing the software programs 7144, it is contemplated that software programs 7144 may be stored on a removable computer medium, such as a hard drive, a computer disk, a CD-ROM, a DVD, a HD, a Blu-Ray DVD, USB flash drive, a SD card, a memory stick, or any other suitable medium; and the software programs 7144 when downloaded to image processing device 7112 may be executed by image processor 7114.

The processor 7114 may be communicatively coupled to the memory device 116, and the processor 7114 may be configured to execute computer executable instructions stored thereon. The processor 7114 may send or receive medical images 7146 to memory 7116. For example, the processor 7114 may receive medical images 7146 from the image acquisition device 7132 via the communication interface 7118 and network 7120 to be stored in memory 7116. The processor 7114 may also send medical images 7146 stored in memory 7116 via the communication interface 7118 to the network 7120 be either stored in database 7124 or the hospital database 7126.

Further, the processor 7114 may utilize software programs 7144 (e.g., a treatment planning software) along with the medical images 7146 and patient data 7145 to create the radiation therapy treatment plan 7142. Medical images 7146 may include information such as imaging data associated with a patient anatomical region, organ, or volume of interest segmentation data. Patient data 7145 may include information such as (1) functional organ modeling data (e.g., serial versus parallel organs, appropriate dose response models, etc.); (2) radiation dosage data (e.g., dose-volume histogram (DVH) information; or (3) other clinical information about the patient and course of treatment (e.g., other surgeries, chemotherapy, previous radiotherapy, etc.).

In addition, the processor 7114 may utilize software programs to generate intermediate data such as updated parameters to be used, for example, by a neural network model; or generate intermediate 2D or 3D images, which may then subsequently be stored in memory 7116. The processor 7114 may subsequently then transmit the executable radiation therapy treatment plan 7142 via the communication interface 7118 to the network 7120 to the radiation therapy device 7130, where the radiation therapy plan will be used to treat a patient with radiation. In addition, the processor 7114 may execute software programs 7144 to implement functions such as image conversion, image segmentation, deep learning, neural networks, and artificial intelligence. For instance, the processor 7114 may execute software programs 7144 that train or contour a medical image; such software 7144 when executed may train a boundary detector, or utilize a shape dictionary.

The processor 7114 may be a processing device, include one or more general-purpose processing devices such as a microprocessor, a central processing unit (CPU), a graphics processing unit (GPU), an accelerated processing unit (APU), or the like. More particularly, the processor 7114 may be a complex instruction set computing (CISC) microprocessor, a reduced instruction set computing (RISC)

microprocessor, a very long instruction Word (VLIW) microprocessor, a processor implementing other instruction sets, or processors implementing a combination of instruction sets. The processor 7114 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, the processor 7114 may be a special-purpose processor, rather than a general-purpose processor. The processor 7114 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processor 7114 may also include graphical processing units such as a GPU from the GeForce®, Quadro®, Tesla® family manufactured by Nvidia™, GMA, Iris™ family manufactured by Intel™ or the Radeon™ family manufactured by AMD™. The processor 7114 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processor 7114 can execute sequences of computer program instructions, stored in memory 7116, to perform various operations, processes, methods that will be explained in greater detail below.

The memory device 7116 can store medical images 7146. In some embodiments, the medical images 7146 may include one or more MRI image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, Cone beam CT, 3D CT, 4D CT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the medical images 146 may also include medical image data, for instance, training images, and ground truth images, contoured images, and dose images. In an embodiment, the medical images 7146 may be received from the image acquisition device 7132. Accordingly, image acquisition device 7132 may include a MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining the medical images of the patient. The medical images 7146 may be received and stored in any type of data or any type of format that the image processing device 7112 may use to perform operations consistent with the disclosed embodiments. The memory device 7116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processor 7114, or any other type of computer device. The computer program instructions can be accessed by the processor 7114, read from the ROM, or any other suitable memory location, and loaded into the RAM for execution by the processor 7114. For example, the memory 7116 may store one or more software applications. Software applications stored in the memory 7116 may include, for example, an operating system 7143 for common computer systems as well as for software-controlled devices. Further, the memory 7116 may store an entire software application, or only a part of a software application, that are executable by the processor 7114. For example, the memory device 7116 may store one or more radiation therapy treatment plans 7142.

The image processing device 7112 can communicate with the network 7120 via the communication interface 7118, which can be communicatively coupled to the processor 7114 and the memory 7116. The Communication interface 7118 may provide communication connections between the image processing device 7112 and radiotherapy system 7100 components (e.g., permitting the exchange of data with external devices). For instance, the communication interface 7118 may in some embodiments have appropriate interfacing circuitry to connect to the user interface 7136, which may be a hardware keyboard, a keypad, or a touch screen through which a user may input information into radiotherapy system 7100.

Communication interface 7118 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 7118 may include one or more digital and/or analog communication devices that permit image processing device 7112 to communicate with other machines and devices, such as remotely located components, via the network 7120.

The network 7120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3(141). Systems S1, S2, and S3 may be identical to image processing device 7112 or may be different systems. In some embodiments, one or more of systems in network 7120 may form a distributed computing/simulation environment that collaboratively performs the embodiments described herein. In some embodiments, one or more systems S1, S2, and S3 may include a CT scanner that obtain CT images (e.g., medical images 7146). In addition, network 7120 may be connected to internet 7122 to communicate with servers and clients that reside remotely on the internet.

Therefore, network 7120 can allow data transmission between the image processing device 7112 and a number of various other systems and devices, such as the OIS 7128, the radiation therapy device 7130, and the image acquisition device 7132. Further, data generated by the OIS 7128 and/or the image acquisition device 7132 may be stored in the memory 7116, the database 7124, and/or the hospital database 7126. The data may be transmitted/received via network 7120, through communication interface 7118 in order to be accessed by the processor 7114, as required.

The image processing device 7112 may communicate with database 7124 through network 7120 to send/receive a plurality of various types of data stored on database 8124. For example, database 8124 may include machine data that is information associated with a radiation therapy device 8130, image acquisition device 8132, or other machines relevant to radiotherapy. Machine data information may include radiation beam size, arc placement, beam on and off time duration, machine parameters, segments, multi-leaf collimator (MLC) configuration, gantry speed, MRI pulse sequence, and the like. Database 8124 may be a storage device and may be equipped with appropriate database administration software programs. One skilled in the art would appreciate that database 8124 may include a plurality of devices located either in a central or a distributed manner.

In some embodiments, database 7124 may include a processor-readable storage medium (not shown). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories, optical and magnetic media. For example, the processor readable storage medium can be one or more volatile, non-transitory, or non-volatile tangible computer-readable media.

Image processor 7114 may communicate with database 7124 to read images into memory 7116 or store images from memory 7116 to database 7124. For example, the database 7124 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DIMCOM) data, etc.) that the database 7124 received from image acquisition device 7132. Database 7124 may store data to be used by the image processor 7114 when executing software program 7144, or when creating radiation therapy treatment plans 7142. Database 7124 may store the data produced by the trained neural network including the network parameters constituting the model learned by the network and the resulting predicted data. The image processing device 7112 may receive the imaging data 7146 (e.g., 2D MRI slice images, CT images, 2D Fluoroscopy images, X-ray images, 3DMRI images, 4D MRI images, etc.) either from the database 7124, the radiation therapy device 7130 (e.g., a MRI-Linac), and or the image acquisition device 7132 to generate a treatment plan 7142.

In an embodiment, the radiotherapy system 7100 can include an image acquisition device 7132 that can acquire medical images (e.g., Magnetic Resonance Imaging (MRI) images, 3D MRI, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of the patient. Image acquisition device 7132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the imaging acquisition device 7132 can be stored within database 7124 as either imaging data and/or test data. By way of example, the images acquired by the imaging acquisition device 7132 can be also stored by the image processing device 7112, as medical image data 7146 in memory 7116.

In an embodiment, for example, the image acquisition device 7132 may be integrated with the radiation therapy device 7130 as a single apparatus (e.g., a MRI device combined with a linear accelerator, also referred to as an "MRI-Linac." Such an MRI-Linac can be used, for example, to determine a location of a target organ or a target tumor in the patient, so as to direct radiation therapy accurately according to the radiation therapy treatment plan 7142 to a predetermined target.

The image acquisition device 7132 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an embodiment, the image acquisition device 7132 can acquire a 2D slice in any orientation. For example, an orientation of the 2D slice can include a sagittal orientation, a coronal orientation, or an axial orientation. The processor 7114 can adjust one or more parameters, such as the thickness and/or orientation of the 2D slice, to include the target organ and/or target tumor. In an embodiment, 2D slices can be determined from information such as a 3D MRI volume. Such 2D slices can be acquired by the image acquisition device 7132 in "near real-time" while a patient is undergoing radiation therapy treatment, for example, when using the radiation therapy device 7130. "Near real-time" meaning acquiring the data in at least milliseconds or less.

The image processing device 7112 may generate and store radiation therapy treatment plans 7142 for one or more patients. The radiation therapy treatment plans 7142 may provide information about a particular radiation dose to be applied to each patient. The radiation therapy treatment plans 7142 may also include other radiotherapy information, such as beam angles, dose-histogram-volume information, the number of radiation beams to be used during therapy, the dose per beam, and the like.

The image processor 7114 may generate the radiation therapy treatment plan 7142 by using software programs 7144 such as treatment planning software, such as Monaco®, manufactured by Elekta AB of Stockholm, Sweden. In order to generate the radiation therapy treatment plans 7142, the image processor 7114 may communicate with the image acquisition device 7132 (e.g., a CT device, a MRI device, a PET device, an X-ray device, an ultrasound device, etc.) to access images of the patient and to delineate a target, such as a tumor. In some embodiments, the delineation of one or more organs at risk (OARs), such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 100 may study the dose distribution not only in the target, but also in the OAR.

In order to delineate a target organ or a target tumor from the OAR, medical images, such as MRI images, CT images, PET images, fMRI images, X-ray images, ultrasound images, radiotherapy portal images, SPECT images and the like, of the patient undergoing radiotherapy may be obtained non-invasively by the image acquisition device 7132 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACO™ manufactured by Elekta AB of Stockholm, Sweden) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45 Gy, ≤55 Gy and <54 Gy, respectively). The result of inverse planning may constitute a radiation therapy treatment plan 7142 that may be stored in memory 7116 or database 7124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 7112 can generate a tailored radiation therapy treatment plan 7142 having these parameters in order for the radiation therapy device 7130 to provide radiotherapy treatment to the patient.

In addition, the radiotherapy system 700 may include a display device 7134 and a user interface 7136. The display device 7134 may include one or more display screens that display medical images, interface information, treatment planning parameters (e.g., contours, dosages, beam angles, etc.) treatment plans, a target, localizing a target and/or tracking a target, or any related information to the user. The user interface 7136 may be a keyboard, a keypad, a touch screen or any type of device that a user may input information to radiotherapy system 7100. Alternatively, the display device 7134 and the user interface 7136 may be integrated into a device such as a tablet computer, e.g., Apple iPad®, Lenovo Thinkpad®, Samsung Galaxy®, etc.

Furthermore, any and all components of the radiotherapy system 7100 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the image processing device 7112, the OIS 7128, the image acquisition device 7132 could be implemented as a virtual machine. Given the processing power, memory, and computational capability available, the entire radiotherapy system 7100 could be implemented as a virtual machine.

Figure 8:
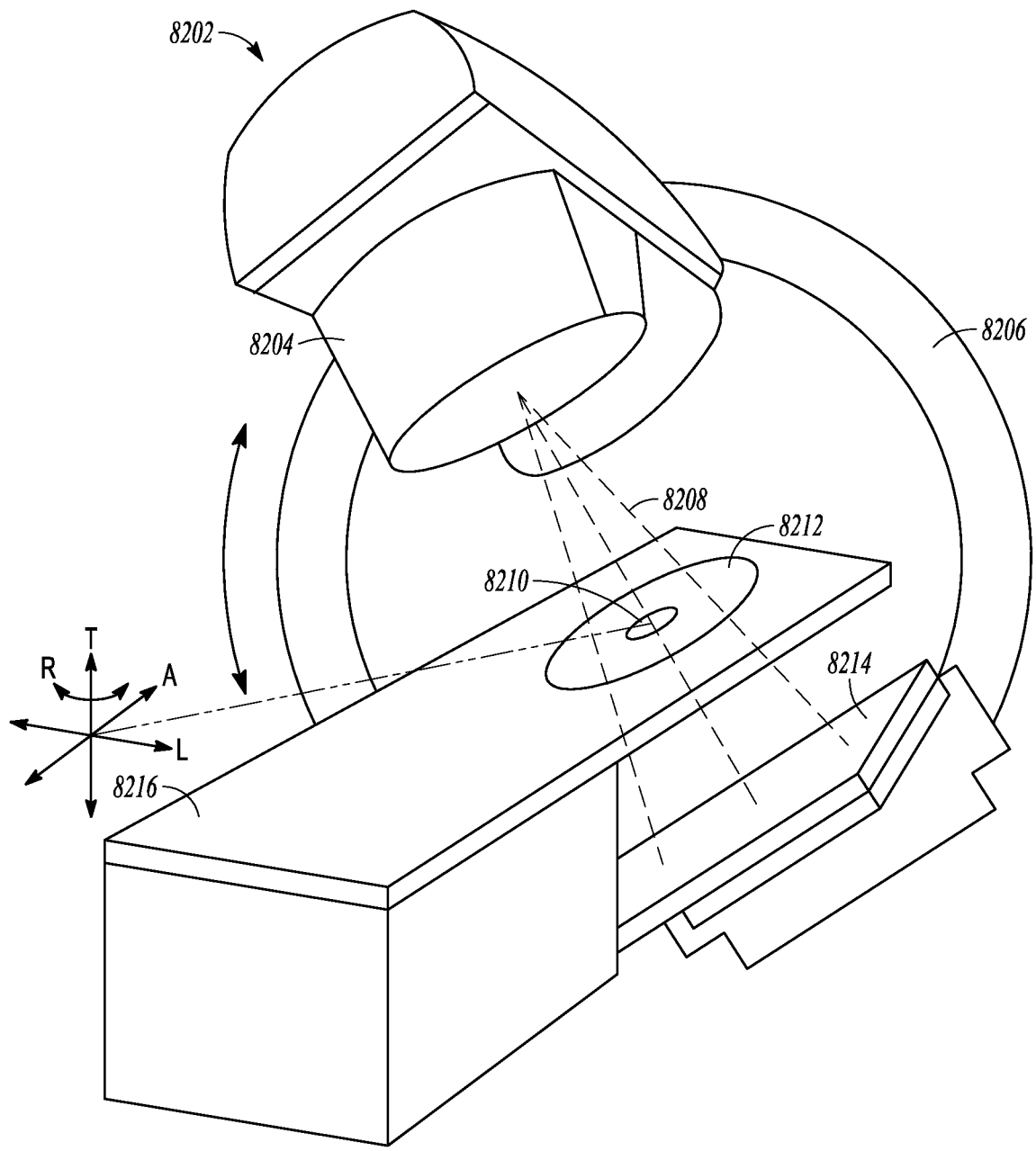
FIG. 8 illustrates an example of a radiation therapy system that can include radiation therapy output configured to provide a therapy beam.

FIG. 8 illustrates an exemplary radiation therapy device 8202 that may include a radiation source, such as an X-ray source or a linear accelerator, a couch 8216, an imaging detector 8214, and a radiation therapy output 8204. The radiation therapy device 8202 may be configured to emit a radiation beam 8208 to provide therapy to a patient. The radiation therapy output 8204 can include one or more attenuators or collimators, such as a multi-leaf collimator (MLC).

In FIG. 8, a patient can be positioned in a region 8212, supported by the treatment couch 8216 to receive a radiation therapy dose according to a radiation therapy treatment plan. The radiation therapy output 8204 can be mounted or attached to a gantry 8206 or other mechanical support. One or more chassis motors (not shown) may rotate the gantry 8206 and the radiation therapy output 8204 around couch 8216 when the couch 8216 is inserted into the treatment area. In an embodiment, gantry 8206 may be continuously rotatable around couch 8216 when the couch 8216 is inserted into the treatment area. In another embodiment, gantry 8206 may rotate to a predetermined position when the couch 8216 is inserted into the treatment area. For example, the gantry 8206 can be configured to rotate the therapy output 8204 around an axis ("A"). Both the couch 8216 and the radiation therapy output 8204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 8216 movements or rotations in order to properly position the patient in or out of the radiation beam 8208 according to a radiation therapy treatment plan. As both the couch 8216 and the gantry 8206 are independently moveable from one another in multiple degrees of freedom, which allows the patient to be positioned such that the radiation beam 8208 precisely can target the tumor.

The coordinate system (including axes A, T, and L) shown in FIG. 8 can have an origin located at an isocenter 8210. The isocenter can be defined as a location where the central axis of the radiation therapy beam 8208 intersects the origin of a coordinate axis, such as to deliver a prescribed radiation dose to a location on or within a patient. Alternatively, the isocenter 8210 can be defined as a location where the central axis of the radiation therapy beam 8208 intersects the patient for various rotational positions of the radiation therapy output 8204 as positioned by the gantry 8206 around the axis A.

Gantry 8206 may also have an attached imaging detector 8214. The imaging detector 8214 preferably located opposite to the radiation source 8204, and in an embodiment, the imaging detector 8214 can be located within a field of the therapy beam 8208.

The imaging detector 8214 can be mounted on the gantry 8206 preferably opposite the radiation therapy output 8204, such as to maintain alignment with the therapy beam 8208. The imaging detector 8214 rotating about the rotational axis as the gantry 8206 rotates. In an embodiment, the imaging detector 8214 can be a flat panel detector (e.g., a direct detector or a scintillator detector). In this manner, the imaging detector 8214 can be used to monitor the therapy beam 8208 or the imaging detector 8214 can be used for imaging the patient's anatomy, such as portal imaging. The control circuitry of radiotherapy device 8202 may be integrated within system 8100 or remote from it.

In an illustrative embodiment, one or more of the couch 8216, the therapy output 8204, or the gantry 8206 can be automatically positioned, and the therapy output 8204 can establish the therapy beam 8208 according to a specified dose for a particular therapy delivery instance. A sequence of therapy deliveries can be specified according to a radiation therapy treatment plan, such as using one or more different orientations or locations of the gantry 8206, couch 8216, or therapy output 8204. The therapy deliveries can occur sequentially, but can intersect in a desired therapy locus on or within the patient, such as at the isocenter 8210. A prescribed cumulative dose of radiation therapy can thereby be delivered to the therapy locus while damage to tissue nearby the therapy locus can be reduced or avoided.

FIG. 8 illustrates generally illustrate an embodiment of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another embodiment, the therapy output can be fixed, such as located in a region laterally separated from the patient, and a platform supporting the patient can be used to align a radiation therapy isocenter with a specified target locus within the patient.

In another embodiment, a radiation therapy device can be a combination of a linear accelerator and an image acquisition device. In some embodiments, the image acquisition device may be an MRI, an X-ray, a CT, a CBCT, a spiral CT, a PET, a SPECT, an optical tomography, a fluorescence imaging, ultrasound imaging, or radiotherapy portal imaging device, etc., as would be recognized by one of ordinary skill in the art.

As used herein, "communicatively coupled between" means that the entities on either of the coupling must communicate through an item therebetween and that those entities cannot communicate with each other without communicating through the item.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The present disclosure also relates to a system for performing the operations described herein. This system may be specially constructed for the required purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in the embodiments illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of the claims.

The present disclosure may be implemented with computer-executable instructions. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

It will be apparent that modifications and variations are possible without departing from the scope of appended claims. As various changes could be made in the above constructions, products, and methods without departing from the scope of the claims, it is intended that all matter contained in the above description and shown in the accompanying drawings shall be interpreted as illustrative and not in a limiting sense.

What is claimed is:

1. A method of validating a radiotherapy treatment plan, comprising:
   producing or obtaining a phantom based upon a medical image of a region of interest of a patient, the region of interest including a target region to be treated by radiotherapy and a non-target region;
   deforming the phantom to model a deformation of at least one of the target region or the non-target region;
   determining a maximum deformation of at least one of the target region or the non-target region for which the radiotherapy treatment plan is valid;
   calculating a warped radiation dose by applying a geometric transformation to a prescribed radiation dose, wherein the prescribed radiation dose defines a spatial distribution of radiation to be delivered to the region of interest;
   generating a radiotherapy treatment plan for configuring a radiotherapy apparatus to deliver the warped radiation dose;
   measuring the radiation dose distribution received by the deformed phantom when radiation is delivered to the deformed phantom by operating the radiotherapy apparatus in accordance with the radiotherapy treatment plan; and
   validating the radiotherapy treatment plan including by comparing the measured radiation dose distribution with the prescribed radiation dose.

2. The method of claim 1, wherein the phantom comprises a smart material that exhibits a change in shape when exposed to an external stimulus, and deforming the phantom includes applying the external stimulus to the smart material.

3. The method of claim 1, wherein the method further comprises:
   acquiring an image of the phantom prior to deforming the phantom;
   acquiring an image of the deformed phantom; and
   calculating the geometric transformation based upon the image of the phantom and the image of the deformed phantom.

4. The method of claim 3, wherein the image of the phantom and the image of the deformed phantom each comprise a plurality of voxels, and wherein calculating the geometric transformation comprises:
   performing deformable image registration to calculate a deformation vector field that maps each voxel in the image of the phantom to a corresponding voxel in the image of the deformed phantom.

5. The method of claim 1, wherein the phantom is produced by an additive manufacturing process.

6. The method of claim 1, wherein producing the phantom comprises positioning a plurality of dosimeters within the phantom.

7. A method of validating a dose warping or other dose mapping technique, comprising:
   accessing a first medical image representing a region of interest of a patient;
   generating a second medical image by applying a first deformation vector field to the first medical image;
   generating, obtaining, or providing first and second phantoms respectively corresponding to the first medical image and the second medical image;
   measuring a corresponding radiation dose distribution received by the first and second phantoms when radiation is respectively delivered thereto by operating the radiotherapy apparatus;
   generating a second deformation vector field including by performing a deformable image registration on the first and second medical images that maps each voxel in the first medical image to a corresponding voxel in the second medical image, and calculating a warped radiation dose including by applying the second deformation vector field;
   calculating the warped radiation dose including by applying the first deformation vector field to a first radiation dose distribution measured using the first phantom, using a dose warping or other dose mapping technique to be validated; and validating the accuracy of the dose warping or mapping technique by comparing the calculated warped dose with a second radiation dose distribution measured using the second phantom.

8. The method of claim 7, wherein at least one of the first and second phantoms is produced by an additive manufacturing process.

9. The method of claim 7, wherein producing at least one of first and second phantoms comprises positioning a plurality of dosimeters within the first and second phantoms.

10. The method of claim 7, comprising validating a cumulative accuracy of the dose warping and the deformable image registration.

11. A method of verifying a radiotherapy treatment session, comprising:
producing a phantom based upon a medical image of a region of interest of a patient, the medical image having been acquired prior to a radiotherapy treatment session in which radiation was delivered to the patient by operating a radiotherapy apparatus in accordance with a radiotherapy treatment plan;
determining a maximum deformation of at least one of the target region or the non-target region for which the radiotherapy treatment plan is valid
measuring the radiation dose distribution received by the phantom when radiation is delivered to the phantom by operating the radiotherapy apparatus in accordance with the radiotherapy treatment plan; and
verifying the radiotherapy treatment session including by comparing the measured radiation dose distribution with dose measurements acquired during the radiotherapy treatment session.

12. The method of claim 11, wherein the phantom is produced by an additive manufacturing process.

13. The phantom of claim 11, wherein producing the phantom comprises locating a plurality of dosimeters within the phantom.

14. A phantom for use in radiotherapy quality assurance, the phantom comprising:
a first portion representing a target region of a patient;
a second portion representing a non-target region of the patient; and
wherein at least one of first or second portions comprises a smart material that exhibits a change in shape when exposed to an external stimulus based on at least one of humidity, temperature, light, electric field, or magnetic field.

15. The phantom of claim 14, wherein the phantom is produced by an additive manufacturing process.

16. The phantom of claim 14, wherein the phantom is produced by the additive manufacturing process based upon a medical image of a region of interest of the patient, the region of interest comprising the target region and the non-target region, such that the first and second portions of the phantom each have a respective shape defined by the shape of the target region and the non-target region, respectively, in the medical image.

17. The phantom of claim 14, wherein the phantom comprises a plurality of dosimeters positioned within the phantom.

* * * * *